United States Patent [19]
Etoh et al.

[11] Patent Number: 5,221,479
[45] Date of Patent: Jun. 22, 1993

[54] FILTRATION SYSTEM

[75] Inventors: Masahiro Etoh; Sumio Ohtani, both of Kanagawa, Japan

[73] Assignee: Fuji Photo Film Co., Ltd., Kanagawa, Japan

[21] Appl. No.: 834,801

[22] Filed: Feb. 13, 1992

[30] Foreign Application Priority Data

Feb. 15, 1991 [JP] Japan .................................. 3-108975
Apr. 18, 1991 [JP] Japan .................................. 3-086934
Apr. 18, 1991 [JP] Japan .................................. 3-086937

[51] Int. Cl.$^5$ ..................... B01D 61/20; B01D 65/08
[52] U.S. Cl. ................................. 210/636; 210/652; 210/798
[58] Field of Search ............... 210/653, 634, 636, 644, 210/649–652, 654, 759, 797, 798

[56] References Cited

U.S. PATENT DOCUMENTS 3,886,066 5/1975 Chen et al. ..................... 210/653

Primary Examiner—Frank Sever
Attorney, Agent, or Firm—Sughrue, Mion, Zinn, Macpeak & Seas

[57] ABSTRACT

A dead-end type filtration system wherein a bulk (or bulk suspension) comprising a fluid containing suspended matters is filtered through a micro-filter membrane to separate the fluid form the suspended matters, back wash is periodically carried out under such conditions that pressure on the transmitted fluid side of the filter membrane is higher than pressure on the bulk side thereof, and back wash liquid together with the suspended matters desorbed form the liter membrane is discharged from the filtration system to the outside, characterized by that said filter membrane has an anisotropic structure where the pore diameters of the filter membrane are changed continuously or discontinuously in the thickness direction of the filter membrane, and the pore diameters on one side of the filter membrane are different from those on other side thereof.

10 Claims, 6 Drawing Sheets

FIG.13
AVERAGE PORE SIZE OF MAXIMUM PORE SIZE LAYERS

FIG.14

FILTRATION SYSTEM

FIELD OF THE INVENTION

This invention relates to a dead-end type filtration system using a filter membrane having an anisotropic structure. More particularly, it relates to a novel dead-end type filtration system wherein back wash is periodically carried out to maintain a large filtrate flux through the membrane. The dead-end type filtration system can be applied to the separation, purification, recovery and concentration of various high-molecular materials, microorganisms, enzyme or fine particles from fluids or suspensions containing the same. Particularly, the system of the present invention can be applied to all cases where fine particles must be separated from fluids containing fine particles to be separated by filtration. For example, the present invention can be applied to the separation of fine particles from various suspensions, fermentation liquors or cultured solutions, the separation of fine particles from pigment suspensions or the separation and removal of clad from condensates in nuclear power generation.

With the rapid development of biotechnology in recent years, the production of biochemical materials by cultivation, fermentation or enzyme reactions has been extensively made in many fields of medical supplies, foods, chemical products, etc. The commercial values of these products can be increased by purification, but the costs of purification are high under the existing conditions. The dead-end type filtration system of the present invention is particularly effective in these fields. For example, the present invention can be applied to various fields including a system wherein a reaction inhibitor is continuously removed from a cultivated liquor to thereby carry out cultivation of high density; a system wherein enzyme is continuously recovered when exoenzyme producing strains are used; a system wherein enzyme is continuously recovered from a solution in which intracellular enzyme producing strains are broken; and a system wherein a biocatalyst is recovered from a cultured liquor obtained by a batch process.

BACKGROUND OF THE INVENTION

Conventional methods for separating suspended matters from a bulk (or bulk suspension) containing the suspended matters by using membranes include reverse osmometry utilizing pressure as a driving force, ultrafiltration method, micro-filtration method, electrodialysis utilizing a potential difference as a driving force and diffusion dialysis utilizing a temperature difference as a driving force. According to these methods, a continuous operation can be conducted, and separation, purification or concentration can be made without causing greatly a change in temperature or pH conditions during the course of separation. These methods enable various materials such as particles, molecules and ions to be separated. Further, since the operation capacity of small-size plants is large according to these methods, the operation can be efficiently carried out, energy required for the separating operation is small and low-concentration bulk suspensions which can be difficultly treated by other separation methods can be treated, and hence the above-mentioned methods are widely used. Membranes which are used in these separation methods include high-molecular membranes mainly composed of an organic high molecular material such as cellulose acetate, cellulose nitrate, regenerated cellulose, polysulfone, polyacrylonitrile, polyamide or polyimide, and porous ceramic membranes which are excellent in durability such as heat resistance and chemical resistance. When colloidal solutions are to be filtered, ultrafiltration membranes are used, and when fine particles are to be filtered, there are used micro-filter membranes having micropores suitable for use in the micro-filtration of fine particles.

With the advance of biotechnology, higher purity performance and higher precision have been demanded as mentioned above, and these systems have replaced conventional centrifugal separation and filtration using diatomaceous earth. The range of fields to which micro-filtration or ultrafiltration technique is applied is increasing because a continuous operation can be made and bulk treatment can be carried out; the filtration can dispense with the addition of a filter aid or a flocculant; separation efficiency is independent of a difference in specific gravity between cell and a suspension, and a clear filtrate can be obtained irrespective of the physical properties of the cultured liquor and the types of cells; high-concentration culture can be carried out and production efficiency can be increased; culture can be carried out a completely closed system without the leakage of cells; cells can be washed after concentration; and scaling up can be easily made and economic advantage are high. Though the filter membranes have many advantages, there are problems that a cake layer is formed by the influence of a concentration polarization to thereby produce a resistance to the flow of the transmitted fluid, and the resistance is increased by the clogging of the filter membrane to thereby cause rapidly and greatly a lowering in filtrate flux through the membrane when fine particles are separated by means of micro-filtration or ultrafilters. This is the greatest cause which obstructs the practical use of micro-filtration or ultrafiltration. Further, membranes used for micro-filtration or ultrafiltration are liable to be contaminated, and hence it is necessary to take a measure to prevent contamination.

Filtration systems include dead-end type filtration system wherein all fluids (bulks) to be filtered are passed through a filter medium (e.g., filter cloth or membrane) and a cake layer to thereby separate fine particles contained in the fluids (bulks). In conventional dead-end type filtration system, a high filtrate flux can be obtained in a stage where a fluid is passed through a filter membrane to thereby capture suspended matters in the inside of the filter membrane and to separate them, but a cake layer is formed in a stage where the suspended matters are captured on the surface of the filter membrane, and the cake layer produces a high filtration resistance when a large amount of a bulk (or bulk suspension) is treated or the specific resistance of the cake layer is extremely high. When such dead-end type filtration is carried out, filtrate flux through the membrane becomes small. For this reason, a dead-end type filtration system with periodic back wash and a crossflow type filtration system has been planned.

In the fields of drain disposal and the filtration of man-made water and pool water, it is known that back wash is carried out to recover the transmissible flux of the clogged filters. However, a system composed of a combination of the dead-end type filtration with back wash is a method which is developed in the field of drain disposal wherein the resistivity of the cake layer is relatively low. Accordingly, when the system as combined is used, the system is ineffective in the filtration of fine particles having a high resistivity, for example, in the separation of cells from fermentation liquors which produce enzyme, beers, wines, Japanese sake, Japanese soys, antibiotics, amino acids and organic acids such as acetic acid and oxalic acid. Filtration methods using a filter aid such as diatomaceous earth or pearlite are most widely used at present to treat these liquors. These methods are a type of a system wherein a block of fine particles of a filter aid is built to form a micro-filtration layer and the filtration is carried out through the fine particle layer. The methods are superior filtration methods which are used for a long time, and the methods are very effective methods for filtering a large amount of a suspension so far. However, these methods have problems in that the work requires many hands and a large amount of industrial waste is formed.

In the crossflow type filtration system, a bulk to be filtered is allowed to flow in parallel with the membrane surface of the filter membrane, the fluid is transmitted through the filter membrane into the opposite side and the flow of the bulk and that of the transmitted fluid cross meet at right angles. Thus, this filtration system is called crossflow type filtration system. In the crossflow type filtration system, the cake layer formed on the surface of the membrane is stripped off by the flow of the bulk in parallel with the filter membrane. Accordingly, the filtrate flux through the membrane is high in comparison with the dead-end type filtration system, and a large amount of the bulk can be directly and continuously separated, purified and concentrated. However, the resistivity of the filtration of the suspended matter is extremely high. Namely, when an ultrafilter or a micro-filtration membrane having a high pure water-filtrate flux, that is, a large fractional molecular weight is used to remove cells or high-molecular materials from the cultured liquor or the fermentation liquor, the filtrate flux through the membrane is rapidly lowered and it is difficult to keep the filtrate flux through the membrane which is high at early stage of the commencement of filtration. Accordingly, when the total amount of the transmitted fluid in the crossflow type filtration system is compared with that of the transmitted fluid in the dead-end type filtration system, the effect obtained by the crossflow type filtration system is small and an economic filtrate flux can not be sufficiently obtained.

The crossflow type filtration system is theoretically a high-degree separation technique as mentioned above. However, the degree of the filtrate flux through the membrane which is the greatest problem in the crossflow type filtration system is only slightly high in comparison with conventional dead-end type filtration system, and there is a problem that a sufficient high filtrate flux through the membrane can not be obtained when the crossflow type filtration system is used as the microfiltration system.

In the embodiments of conventional separation of the suspended matter from the fluids, there are problems that not only the filtrate flux through the membrane is lowered by the cake layer formed on the surface of the membrane or the clogging of the membrane with the passage of the filtration time, but also the activity of cells is lost by a shearing force in the recycling of the bulk even when the crossflow type filtration system is used in place of conventional centrifugal separation or filtration system using diatomaceous earth, for example, in the separation of cells from the fermentation liquors.

As a method for increasing the transmitted flux, there has been conventionally tried so-call back wash wherein a cake layer or a deposit layer accumulated on the surface of the membrane on the bulk side of the filter membrane is intermittently removed by intermittently stopping the inflow of the bulk into the filter membrane, closing a valve provided on the transmitted fluid side of the filter membrane, intermittently removing pressure vertically applied to the surface of the filter membrane or reducing said pressure, or allowing the fluid to flow from the transmitted fluid side to the bulk side by applying pressure from the transmitted fluid side of the filter membrane. When a resistivity to the filtration of the suspended matter is low, the suspended matter accumulated to the filter membrane can be easily desorbed by back wash. However, in the case of high molecular components or cells which have high resistivity to the filtration of the suspended matter and high adhesion to the filter membrane, there are problems that they can not be sufficiently removed from the filter membrane by back wash, and the filtrate flux through the membrane can not be sufficiently recovered. In addition, there are problems that when the suspended matter desorbed from the filter membrane is left behind in the filtration system in carrying out back wash, the concentration of the suspended matter in the bulk is gradually increased, and optionally the viscosity of the bulk is increased with the result that the filtrate flux through the membrane is gradually lowered and the filtrate flux can not be sufficiently recovered even when back wash is carried out.

As a method for preventing the activity of cells from being lowered, there is conventionally carried out a method wherein a shearing force is reduced by lowering a circulating flow rate in the case of the crossflow type filtration system. However, when the shearing force is reduced, the effect of the crossflow type filtration system is reduced. Hence, there is a problem that the filtrate flux through the membrane is lowered when the filtration is carried out so as not to allow the activity of the cells to be practically lowered. Further, there is a problem that when a pump having a low shearing force such as a diaphragm pump is used to reduce the breakage of the cells, the pulsation of the pump is large and the effect of the crossflow type filtration system is reduced.

The present invention is intended to solve the problems associated with the prior art as mentioned above.

SUMMARY OF THE INVENTION

An object of the present invention is to provide a novel dead-end type filtration system which has a practical high filtrate flux through the membrane and can prevent the activity of cells, etc. from being lowered.

The above-described object of the present invention has been achieved by providing a dead-end type filtration system wherein a bulk (or bulk suspension) comprising a fluid containing suspended matters is filtered through a micro-filter membrane to separate the fluid from the suspended matters, back wash is periodically carried out under such conditions that pressure on the transmitted fluid side of the filter membrane is higher than pressure on the bulk side thereof, and the back wash liquid together with the suspended matters desorbed from the filter membrane is discharged from the filtration system to the outside, characterized by that said filter membrane has an anisotropic structure where the pore diameters of the filter membrane are changed continuously or discontinuously in the thickness direction of the filter membrane and the pore diameters on one side of the filter membrane are different from those on other side thereof.

Numerals in Fig. represent the following matters.
1: Flow of bulk in dead-end type filtration
2: Flow of transmitted fluid in dead-end type filtration
3: Migrating direction of suspended matters in dead-end type filtration
4: Suspended matters accumulated on filter membrane
5: Filter membrane
6: Flow of bulk in crossflow type filtration
7: Flow of transmitted fluid in crossflow type filtration
8: Migrating direction of suspended matters in crossflow type filtration
9: Suspended matters accumulated on filter membrane
10: Filter membrane
11: Inlet for bulk
12: Outlet for transmitted fluid
13: Inlet for back wash liquid
14: Outlet for waste liquid
15: Filter
16: Filter membrane
17: Gas inlet
18: Pressure gauge
19: Pump
20: Sterization filter
21: Electromagnetic value
22: Cross-sectional view of filter membrane
23: Suspended matters
24: Cross-sectional view of filter membrane
25: Suspended matters
26: Present invention
27: Crossflow type filtration with back wash
28: Conventional dead-end filtration
29: Present invention
30: Crossflow type filtration with back wash
31: Conventional dead-end filtration
32: Composite filter membrane of the present invention
33: Anisotropic membrane wherein the larger pore is positioned on the bulk side
34: Filter housing
35: Filtration pump
36: Back wash pump
37: Bulk liquid
38: Transmitted liquid storage tank
39: Back wash liquid
40: Gas inlet
41: Outlet for back wash liquid

DETAILED DESCRIPTION OF THE INVENTION

The present invention will be illustrated in more detail below.

The dead-end type filtration system using an anisotropic filter membrane can be applied to all cases where fine particles must be separated from fluids containing the same by filtration, for example, various high-molecular materials, microorganisms, yeast or fine particles must be separated from fluids containing the same or suspensions containing the same by filtration, and such fluids must be purified, recovered or concentrated through filtration. Particularly, the present invention is effective in the filtration of suspended matters having an extremely high resistivity to filtration such as the separation, concentration or recovery of enzyme, microorganism or cells from fermentation liquors or cultured liquors.

The filter membrane used in the filtration system of the present invention must have pores having a pore size which can inhibit the passage of suspended matters therethrough. In the case of micro-filter membranes, filter membranes having pores having a pore size of 0.05 to 10 μm are generally used. When filtration is carried out in a short period of 0.5 to 3 minutes by these micro-filter membranes, the total amount of filtered liquor is greatly affected by the structures of the filter membranes. The filter membranes can be classified into so-called isotropic membrane type wherein the pore sizes of micropores existing in the interior of the membrane are substantially uniform and the pore sizes of micropores on both surfaces thereof are substantially uniform; and so-called anisotropic membrane type wherein the pore sizes of micropores are changed continuously or discontinuously in the thickness direction of the membrane and the pore sizes on one surface side thereof are different from those on other surface side thereof. The isotropic membranes are described in JP-A-58-98015 (the term "JP-A" as used herein means an "unexamined published Japanese patent application"), and have disadvantages in that the whole of the membrane has a high resistance to the flow of the fluid in conducting filtration; flow rate is low (namely, flow rate per unit area/unit time/unit pressure difference being low); the membrane is liable to be clogged; filtration life is short; and the membrane does not have blocking resistance. The anisotropic membranes are described in JP-B-55-6406 (the term "JP-B" as used herein means an "examined Japanese patent application"), JP-A-56-154051 and JP-A-63-139930, and have a layer having pores having a small pore size called a dense layer on one surface side of the membrane or in the interior thereof, and a layer having pores having a relatively large pore size or extremely large voids from the interior of the membrane to other surface side thereof. When the isotropic membrane is used or when the bulk is fed to the smaller pore size side of the anisotropic membrane, the suspended matter is captured on the surface of the filter membrane, while when the bulk is fed to the larger pore size side of the anisotropic membrane, the suspended matter is captured in the interior thereof. Namely, when the suspended matter is captured on the surface of the filter membrane, the captured suspended matter becomes a very large resistance to filtration, the filtrate flux is rapidly lowered and as a result, the total amount of the filtered fluid is reduced. On the other hand, when a filter membrane having such a structure that the pore sizes of pores are changed continuously or discontinuously in the thickness direction of the membrane and one surface side of the membrane is different in the pore sizes of the pores from other surface side thereof, that is, so-called anisotropic membrane is used in such a way that the larger pore size surface side thereof is positioned as the bulk side, the suspended matter can be captured in the interior of the filter membrane, whereby the total amount of the filtered fluid can be increased. In the present invention, the average pore size on the surface sides of the membrane and in the interior thereof is calculated from electron micrograph.

When the average pore size of the pores on the larger pore size surface side of the anisotropic membrane is extremely larger than the average pore size of the pores of the dense layer having the smallest pore size, the suspended matter is uniformly dispersed in the cross-sectional direction of the dense layer in the interior of the membrane and concentratedly captured in the area of the dense layer. Hence, the characteristics of the anisotropic membrane cannot be displayed, and the filtration ends in the same results as in the isotropic membrane wherein the suspended matter is captured on the surface of the membrane. Namely, the membrane must have an anisotropic structure suitable for allowing the suspended matter to be dispersed in the interior of the membrane and captured to display the feature of the anisotropic membrane. The anisotropic structure is defined by the ratio of the average pore size on the large pore size surface side to that of the dense layer in both cases where the dense layer exists on one surface side of the membrane and in the interior thereof. In the micro-filter membrane, the average pore size of the dense layer is generally 0.05 to 10 $\mu$m as mentioned above. In the case of the anisotropic membrane, the average pore size on the larger pore size surface side is generally 1 to 100 $\mu$m, and the average pore size on the larger pore size surface side is 1 to 1000 times that of the dense layer. In the preferred anisotropic structure for obtaining a large amount of filtered fluid, the average pore size on the large pore size surface side is at least twice, but not larger than 500 times, preferably at least 5 times, but not larger than 50 times that of the dense layer. It is preferred that the structure ranging from the larger pore size surface side to the dense layer is such that the average pore size is uniformly changed to disperse uniformly the suspended matter in the interior of the membrane. It is preferred that the thickness of the filter membrane is thicker to improve an effect of capturing the suspended matter. The thickness of the filter membrane is generally 20 to 1000 $\mu$m, preferably 100 to 300 $\mu$m from the view points of the strength and handling properties of the filter membrane.

Suspended particles in the fermentation liquors are agglomerated particles comprising fungi such as bacteria, yeast and hypha, ingredients in culture medium and protein and polysaccharide originating from fermentation metabolite. With regard to the particle size thereof, the particles widely ranges from submicron particles having a particle size of as small as about 0.1 $\mu$m to large particles having a particle size of several tens of $\mu$m. The average particle size, the particle size distribution and the concentration vary depending on the types of the fermentation liquors. Further, the type of filtration varies depending on products. Hence, the minimum particle size to be subjected to removal is not defined. For example, in the case of beer, the particle size is mostly 2 to 5 $\mu$m, and the concentration of the suspended matter is 0.1 to 1 g/l. Such beer must be filtered through a micro-filter membrane having an average pore size of not larger than 1.5 $\mu$m to obtain a clear liquid. When there is used a membrane having pores uniformly distributed in the thickness direction thereof such as a nylon membrane prepared by the method described in JP-A-55-8887, all of particles are trapped on the surface of the membrane and the clogging of the membrane is immediately caused. On the other hand, when filtration is carried out through a micro-filter membrane having an anisotropic structure when the average pore size on the inlet side of filtration is 4 to 30 $\mu$m, and the average pore size of the minimum pore size layer in the interior of the membrane is 0.3 to 3 $\mu$m, the property with regard to clogging can be greatly improved. Further, it was found that quite unfiltered premature beer can be practically filtered when there is conducted filtration with periodic back wash in which filtration is carried out through the filter membrane having an anisotropic structure mentioned above for 5 to 60 minutes, back wash is then carried for several seconds and these operations are repeatedly carried out.

Alcoholic beverages such as beer and Japanese sake are filtered to clarify liquors and remove various bacteria such as hiochi bacteria (*Bacillus saproqenes*). The average pore size of about 1.5 $\mu$m, concretely 0.8 to 3

μm in the minimum pore size layer of the anisotropic membrane will suffice only for the former purpose. However, when the latter purpose must also be achieved, the average pore size of the minimum pore size layer of the anisotropic membrane must be reduced to from 0.3 to 0.6 μm. It is advantageous that the average pore size of the minimum pore size layer of the anisotropic membrane is as large as 2 to 10 μm when the materials to be filtered are bacteria which form large masses by intertwining, such as moulds, as in the fermentation of antibiotics, or no trouble is caused in subsequent stages even though a small amount of fermentation bacterium drops out and is introduced into the filtrate. Generally, it is necessary that the average pore size of the minimum pore size layer of the anisotropic membrane is not larger than 0.8 times the minimum particle size of the material to be removed.

The optimum pore size on the inlet side of filtration varies depending on the volume-average particle size of suspended particles in the bulk to be filtered and the particle size distribution thereof. Generally, the pore size is 2 to 20 times the volume-average particle size of the suspended particles. In many cases, the optimum pore size is in the range of 3 to 15 times the volume-average particle size.

When a filter membrane having a composite structure obtained by integrating a porous membrane with nonwoven fabric or a network structural material is used in such a way that the nonwoven fabric side or the network structure side is positioned as the bulk side, the trapping of the suspended matter can be further increased. Particularly, when the particle size distribution of the suspended matter is wide, the effect of trapping the suspended matter is high because the suspended matter having a large particle size can be trapped in the interior of nonwoven fabric and the suspended matter having a small particle size can be trapped in the interior of the porous membrane. Further, when back wash is periodically carried out, there is caused a problem that a high load is applied to the filter membrane during back wash and the membrane is cracked when the strength of the membrane is low. However, when the porous membrane is combined with nonwoven fabric, the strength of the membrane can be extremely increased. The integration of the porous membrane with nonwoven fabric or the network structural material may be made by heat-sealing them dotwise or linewise with an adhesive, but a porous structure may be formed by casting a solution (which is to be molded into a filter membrane) directly on nonwoven fabric or the network structural material to allow a part of the porous membrane to intrude into nonwoven fabric as described in JP-B-45-13931.

In carrying out back wash in the dead-end type filtration of the present invention, the use of a liquid gives a larger effect than that of gas. When the inclusion of foreign substances from the outside is to be avoided, the transmitted liquid can be used as the back wash liquid. Further, when the amount of the transmitted fluid is to be prevented from being reduced by a portion of the transmitted fluid, said portion being used for back wash, it is preferred that a fresh back wash liquid is supplied from the outside and back wash is carried out with a required amount of the back wash liquid. Any of back wash liquids can be basically used, so long a the back wash liquids fed from the outside cause neither a lowering in the characteristics of the filter membrane nor a change in the characteristics of the bulk. Generally, it is preferred that sterilized water is used when the bulk is an aqueous solution. It is also preferred that dehydration is carried out by gas when any back wash water is not to be left behind in the filtration system after back wash. When back wash is carried out after the filtrate flux through the membrane is extremely lowered, the recovery of the filtrate flux through the membrane after back wash becomes poor. This is because the suspended matter penetrates deeply into the interior of the filter membrane, the accumulated suspended matter is compacted or the suspended matter is firmly bonded to the filter membrane by long-time filtration, and it is impossible to completely remove the suspended matter accumulated during back wash. For this reason, it is preferred that back wash is carried out before the transmitted flow rate reaches 1/1000 of that at the initial stage of the filtration when constant pressure filtration is carried out. It is more preferred that back wash is carried out before the transmitted flow rate reaches 1/10 of that at the initial stage of the filtration to obtain a higher transmitted flow rate. When constant rate filtration is carried out, it is preferred that back wash is carried out before a pressure difference between both sides of the filter membrane reaches 100 times that at the initial stage of the filtration because when back wash is carried out after a pressure difference between both sides of the filter membrane is raised, the recovery of the pressure difference after back wash, that is, the washability of the filter membrane becomes poor. More preferably, back wash is carried out before the pressure difference reaches 10 times that at the initial stage of the filtration. Accordingly, a time taken until back wash after the initiation of the filtration is short, and it is preferred that when the resistivity of the suspended matter is high, back wash is carried out after filtration is carried out for at least 0.5 minutes, but not longer than 3 minutes. When a large amount of the back wash liquid is passed through the filter membrane at a high transmitted flow rate, washability is increased. However, when back wash is carried out for a long period of time by increasing the filtrate flux of the back wash liquid, not only the amount of the back wash liquid is increased, but also the ratio of back wash time to filtration time is increased and the average filtrate flux is practically lowered. Accordingly, it is preferred the filtration factors such as flow rate and time are so set that a sufficient transmitted flow rate can be recovered. Preferably, the transmitted flow rate is at least $1 \times 10^{-4}$ m$^3$/m$^2$/sec and time is at least one second, but not longer than 30 seconds.

The dead-end type filtration system of the present invention will be illustrated by referring to the accompanying drawings.

Figures 1, 2, 3:
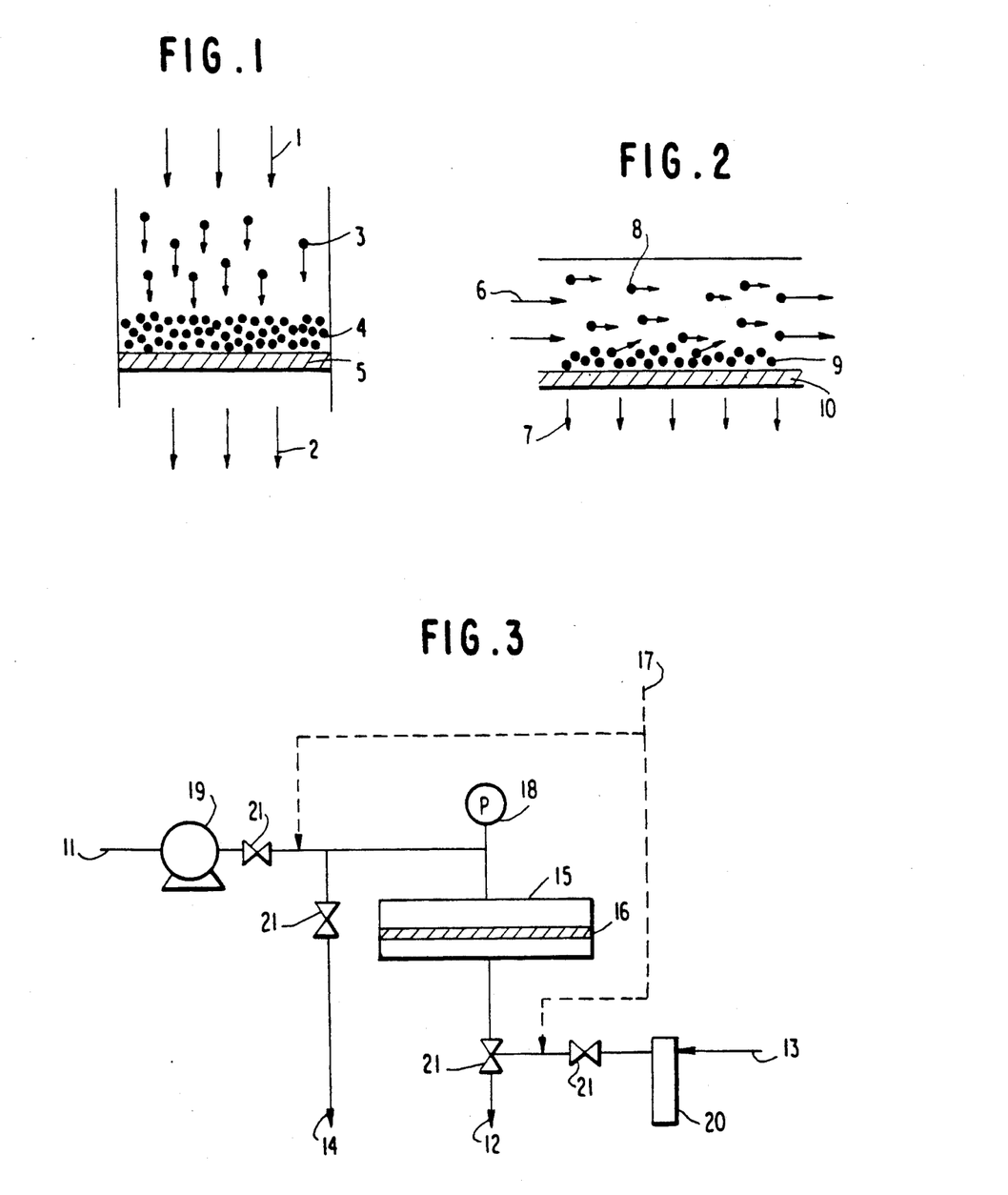
FIG. 1 illustrates the accumulated state of suspended matters in a conventional dead-end type filtration.
FIG. 2 illustrates the accumulated state of suspended matters in a conventional crossflow type filtration.
FIG. 3 is a flow sheet showing a dead-end type filtration system wherein back wash is periodically carried out according to the present invention.

FIG. 1 shows the state of the suspended matter accumulated on the filter membrane when a conventional dead-end type filtration is carried out. The amount of the accumulated suspended matter is increased, and the filtrate flux finally approaches zero.

FIG. 2 shows the state of the suspended matter accumulated on the filter membrane when crossflow type filtration is carried out. The amount of the suspended matter accumulated at the initial stage of the filtration is gradually increased, but the amount of the suspended matter accumulated is made a given value by the shearing force of the bulk and the filtrate flux finally approaches a given value.

FIG. 3 is a flow sheet illustrating the dead-end type filtration system according to the present invention. In this system, after filtration is carried out for a given period of time, sterilized water is allowed to flow from the transmitted fluid side to the bulk side, and the sterilized water together with the suspended matter desorbed from the filter membrane is discharged. Subsequently, the sterilized water left behind in the filtration system is discharged by gas and the filtration is again carried out. When this cycle is repeated, a high filtrate flux can be maintained without increasing the concentration of the suspended matter in the bulk.

Figure 4:
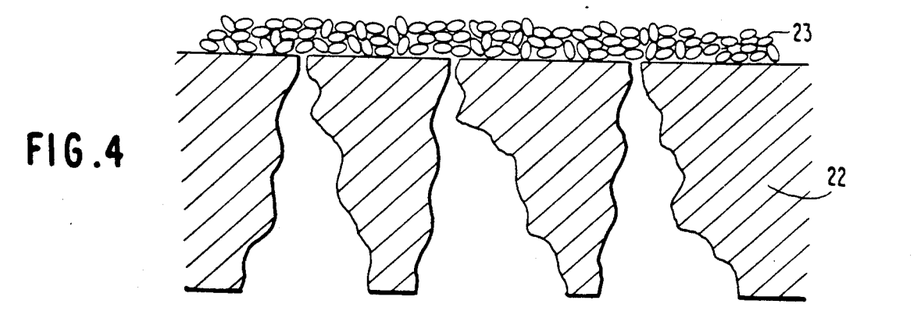
FIG. 4 is a sectional view of the filter membrane illustrating a state where the suspended matters are accumulated on the surface of the filter membrane.
Figure 5:
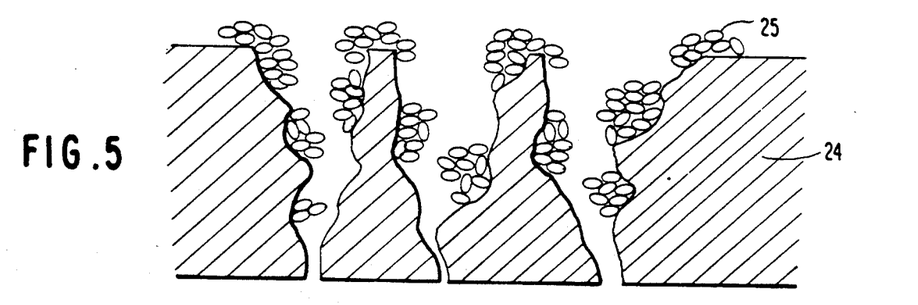
FIG. 5 is a sectional view of the anisotropic membrane according to the present invention illustrating a state where the suspended matters are accumulated from the larger pore size side toward the inside of the membrane.

FIG. 4 is a cross-sectional view of the filter membrane illustrating the case where the suspended matter is captured (trapped) on the surface of the filter membrane. FIG. 5 illustrates the structure of the filter membrane according to the present invention. According to the structure of the filter membrane of the present invention, the suspended matter can be captured in the interior of the membrane. Hence, the suspended matter does not form a remarkably high resistance and as a result, a large amount of the filtered fluid can be obtained.

The present invention is now illustrated in greater detail by reference to the following examples which, however, are not to be construed as limiting the present invention in any way.

EXAMPLE 1

Figure 6:
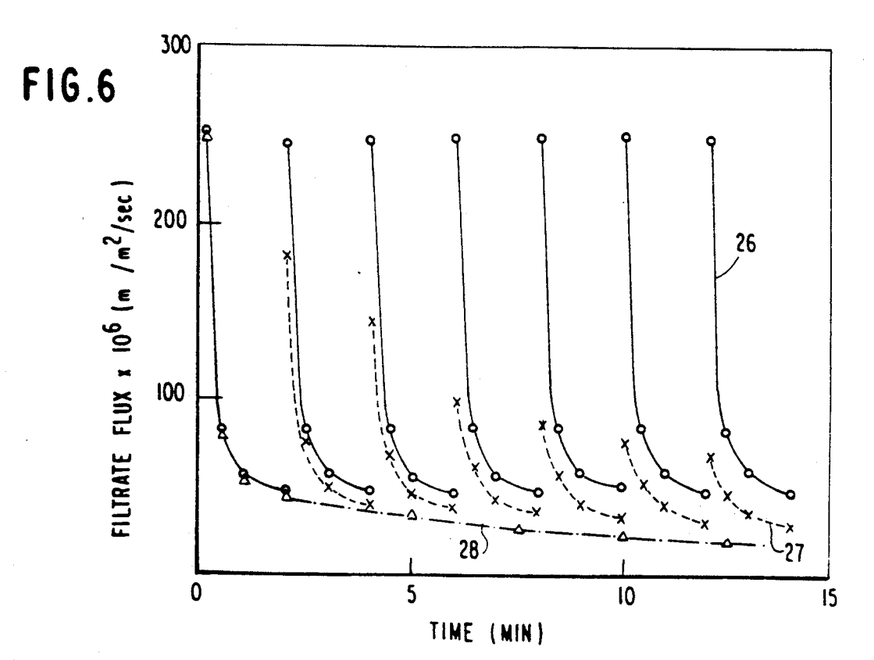
FIG. 6 is a graph showing the comparison of filtrate fluxes when a cultured liquor of E. coli is filtered by means of the dead-end type filtration with periodical back wash according to the present invention, the crossflow type filtration with back wash and conventional dead-end filtration.

*E. Coli* (IFO 3301) was placed in a culture medium containing 10 g/l of glucose, 5 g/l of polypeptone, 5 g/l of yeast extract and 5 g/l of sodium chloride, and cultured for 18 hours by means of shaking culture to obtain a bulk solution to be filtered. The culture conditions were such that the temperature was 37° C. and the pH was 7.0. The bulk solution was filtered through a micro-filter membrane having a nominal pore size of 0.2 $\mu$m by means of the dead-end type filtration wherein back wash was periodically carried out according to the present invention. The filter used had an effective membrane area of 100 cm$^2$. The experimental conditions were such that the pressure difference was $0.5 \times 10^5$ Pa, the temperature of the solution was 25° C., the back wash flux was $1 \times 10^{-3}$ m$^3$/m$^2$/sec, the back wash time was 3 seconds, and the back wash liquid was sterilized water. FIG. 6 is a graph showing the results obtained by carrying out the filtration according to the present invention together with the results obtained by carrying out back wash with the transmitted solution as the back wash liquid according to the crossflow type filtration system (operation time being 120 seconds, and back wash time being 3 seconds) (Comparative Example) and the results obtained by carrying out conventional dead-end type filtration (Comparative Example).

It is apparent from these results that the filtrate flux approaches zero with time in a conventional dead-end type filtration, and the filtrate flux is gradually reduced without being sufficiently recovered by back wash in the crossflow type filtration with back wash, a high filtrate flux value can be retained in the dead-end type filtration with periodic back wash according the the present invention.

EXAMPLE 2

Figure 7:
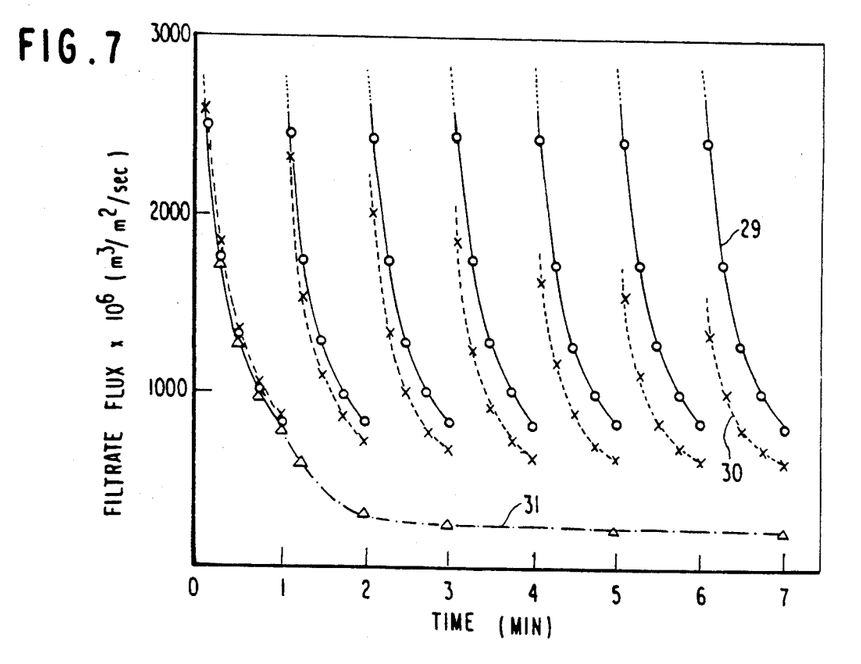
FIG. 7 is a graph showing the comparison of filtrate fluxes when beer containing agglomerated protein is filtered by means of the dead-end type filtration with periodic back wash according to the present invention, the crossflow type filtration with back wash and conventional dead-end type filtration.

In commercially available beer was dissolved 20 ppm of tannic acid, and protein was agglomerated to obtain a suspension. The suspension was filtered through an anisotropic micro-filter membrane having a nominal pore size of 2.0 $\mu$m by means of dead-end type filtration with periodic back wash according to the present invention wherein the large pore size surface side was positioned as the suspension side. The anisotropic membrane was prepared in the following manner. A raw solution containing 15 parts of polysulfone (P3500 manufactured by Amoco Co.), 15 parts of polyvinyl pyrrolidone and 3 parts of water dissolved in 70 parts of N-methylpyrrolidone was cast with a solution film thickness of 180 $\mu$m on a glass sheet by using a cast coater, and the surface of the solution film was exposed to air at a rate of 2 m/sec, said air being conditioned at 25° C. and 45% RH. Immediately thereafter, the film was immersed in a 25° C. coagulating bath filled with water to thereby obtain the membrane. The filter used had an effective membrane area was 100 cm$^2$. The experimental conditions were such that the pressure difference was $0.5 \times 10^5$ Pa the solution temperature was 2° C., the filtration time was 60 seconds, the back wash flux was $5 \times 10^{-3}$ m$^3$/m$^2$/sec, the back wash time was 4 seconds, and the back wash liquid was sterilized water. FIG. 7 is a graph showing the results obtained by carrying out filtration according to the filtration system of the present invention together with the results obtained by carrying out back wash with the transmitted solution as the back wash liquid according to crossflow type filtration system (operation time being 60 seconds and back wash time being 3 seconds) (Comparative Example) and the results obtained by conventional dead-end type filtration (Comparative Example). It is apparent from these results that the filtrate flux approaches zero with time in a conventional dead-end type filtration and the filtrate flux is gradually reduced without being sufficiently recovered in the crossflow type filtration with back wash, while a high filtrate flux value can be retained in the dead-end type filtration with periodic back wash according to the present invention.

EXAMPLE 3

In commercially available beer was dissolved 20 ppm of tannic acid, and protein was agglomerated to form a suspension. The suspension was filtered through a micro-filter membrane having different anisotropy (wherein the dense layer had an average pore size of 2.0 m) by means of the dead-end type filtration with periodic back wash according to the present invention wherein the larger pore size surface side of the membrane was positioned as the suspension side. The anisotropic membrane was prepared by immersing the cast and exposed film in coagulating baths filled with water at different temperatures of (1) 3° C., (2) 20° C., (3) 35° C., (4) 45° C., or (5) 80° C. according to the method of Example 2. The membrane prepared was an anisotropic membrane having a dense layer therein. The relationship between the average pore size of the larger pore size surface side and the average pore size of the dense layer is shown in Table 1 described hereinafter.

TABLE 1

|  | A Average pore size of the larger pore size side ($\mu$m) | B Average pore size of dense layer ($\mu$m) | Pore size ratio A/B |
|---|---|---|---|
| Anisotropic membrane (1) | 4.0 | 2.0 | 2 |
| Anisotropic membrane (2) | 10.0 | 2.0 | 5 |
| Anisotropic membrane (3) | 100 | 2.0 | 50 |
| Anisotropic membrane (4) | 200 | 2.0 | 100 |
| Anisotropic | 1000 | 2.0 | 500 |

TABLE 1-continued

| | A Average pore size of the larger pore size side (μm) | B Average pore size of dense layer (μm) | Pore size ratio A/B |
|---|---|---|---|
| membrane (5) Isotropic | 2.0 | 2.0 | 1 |

Figure 8:
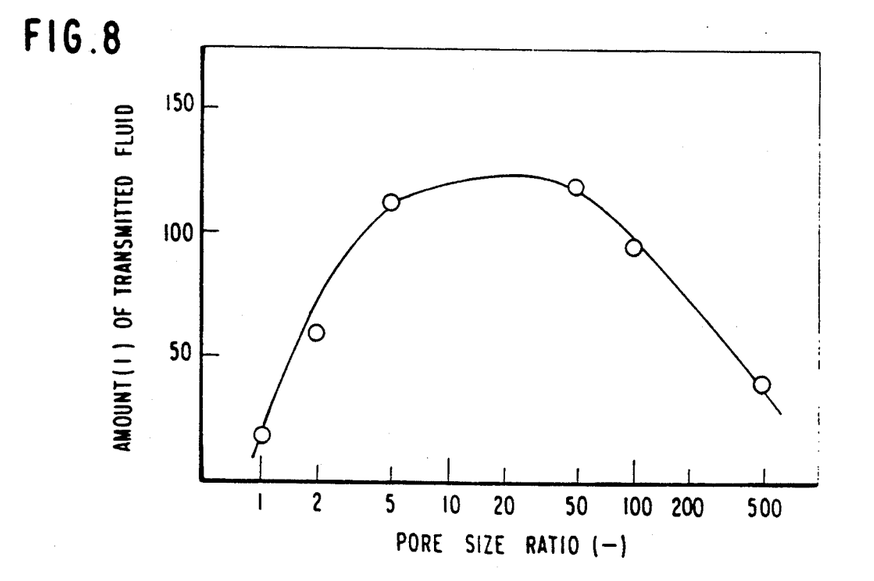
FIG. 8 is a graph showing a difference in the total amount of filtered fluid when beer containing agglomerated protein is filtered by means of the filtration system according to the present invention wherein the surface side having a larger pore size in the filter membrane having different anisotropy is the stock fluid side.

The filter used had an effective membrane area of 100 cm$^2$. The experimental conditions were such that the pressure difference was 0.5×105 Pa, the solution temperature was 2° C., the filtration time was 60 seconds, the back wash flux was 5×10$^{-3}$ m$^3$/m$^2$/sec, the back wash time was 4 seconds, and the back wash liquid was sterilized water. FIG. 8 is a graph showing the results of the total amount of the filtered solution after filtration for 4 hours when the dead-end type filtration was conducted by using an isotropic membrane and the membrane prepared above. It was found that the total amount of the filtered solution is large when the average pore size of the larger pore size surface side of the anisotropic membrane is at least twice, but not larger than 1000 times the average pore size of the.

EXAMPLE 4

Figure 9:
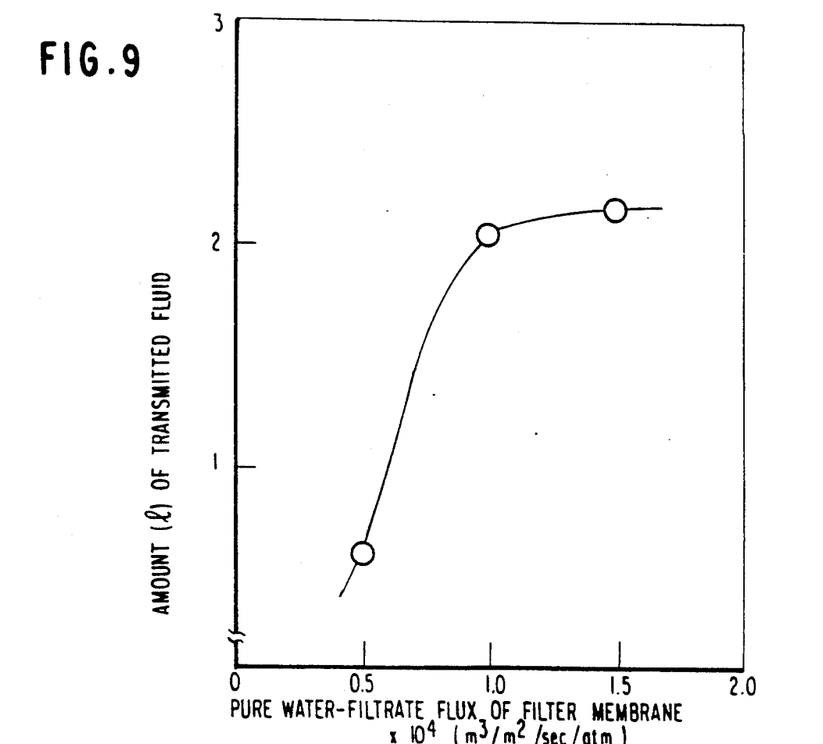
FIG. 9 is a graph showing the results obtained by filtering a cultured liquor of E. coli through filter membranes giving different pure water-transmitted (or filtrate) fluxes according to the filtration system of the present invention.

The bulk solution of Example 1 was used as a suspension. The suspension was filtered through each of three anisotropic filter membranes having a nominal pore size of 0.2 μm (which were different in pure water-filtrate flux) by means of the dead-end filtration with periodic back wash according to the present invention wherein the larger pore size surface side was positioned as the suspension side. The anisotropic membrane was prepared in the following manner. A solution containing 15 parts of polysulfone (P3500 manufactured by Amoco Co.), 15 parts of polyvinyl pyrrolidone and 2 parts of water dissolved in 70 parts of N-methylpyrrolidone was cast with a liquid thickness of 180 μm on a glass plate by means of a cast coater, and the surface of the liquid film was exposed to air at a rate of 2 m/sec for one second, two seconds and three seconds, respectively said air being conditioned at 25° C. and 45% RH. Immediately thereafter, each film was immersed in a coagulating bath filled with water to prepare each membrane. The pure water filtrate fluxes at 25° C. of these three filter membranes were 0.5×10$^{-4}$ m$^3$/m$^2$/sec/atm, 1.0×10$^{-4}$ m$^3$/m$^2$/sec/atm and 1.5×10$^{-4}$ m$^3$/m$^2$/sec/atm, respectively. The filter used had an effective membrane area of 100 cm$^2$. The experimental conditions were such that the pressure difference was 0.5×105Pa, the liquid temperature was 2° C., the back wash flux was 5×10$^{-3}$ m$^3$/m$^2$/sec, the back wash time was 4 seconds, and the back wash liquid was sterilized water. FIG. 9 is a graph showing the comparison of the total amounts of the transmitted solutions after filtration for 4 hours. It is apparent that when the pure water filtrate flux of the filter membrane exceeds 1×10$^{-4}$ m$^3$/m$^2$/sec/atm, the recovery of the filtrate flux by back wash is improved and a considerably large amount of the transmitted solution can be obtained.

EXAMPLE 5

Figure 10:
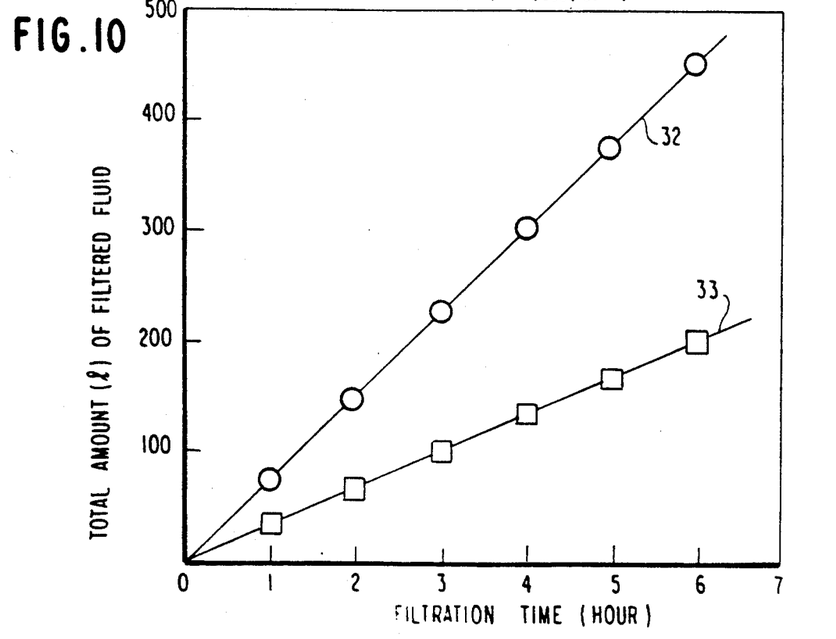
FIG. 10 is a graph showing the results obtained by filtering beer containing agglomerated protein through a composite membrane obtained by integrating a porous membrane with nonwoven fabric according to the filtration system of the present invention.

In commercially available beer was dissolved 20 ppm of tannic acid, and protein was agglomerated to form a suspension. The suspension was filtered through an anisotropic composite membrane having a nominal pore size of 2.0 μm by the dead-end type filtration with periodic back wash according to the present invention. Said anisotropic composite membrane was prepared from polypropylene nonwoven fabric having a weight of 1 g/m$^2$ and a thickness of 0.2 mm and a membrane obtained by casting the solution of Example 2 into a membrane under the same conditions as in Example 2. In the filtration, the nonwoven fabric side was positioned as the suspension side. The filter used had an effective membrane area of 100 cm$^2$. The experimental conditions were such that the pressure difference was 0.5×105 Pa, the temperature of the solution was 2° C., the filtration time was 60 seconds, the back wash flux was 5×10$^{-3}$ m$^3$/m$^2$/sec, the back wash time was 4 seconds and sterilized water was used as the back wash liquid. FIG. 10 is a graph showing a change in the total amount of the transmitted liquid with time together with the results obtained by using the filter membrane used in Example 2. When the composite membrane obtained by integrating the porous membrane with nonwoven fabric is used, an amount of the transmitted liquid can be further increased.

EXAMPLE 6

15 parts of polysulfone (P-3500 manufactured by Amoco), 70 parts of N-methyl-2-pyrrolidone, 2 parts of water and 15 parts of polyvinyl pyrrolidone were uniformly dissolved to prepare a solution. The solution was cast in such an amount as to give a thickness of 180 μm. The cast film was exposed to air at 25° C. and 60% RH for 6 seconds and immersed in water at 15° C. to obtain an anisotropic micro-filter membrane having a dense layer in the interior thereof. The pore size of the membrane was measured according to ASTM-F316. It was found that the average pore size was 1.4 μm. The cross-sectional SEM photograph of the membrane was taken. The average pore size of the minimum pore size layer was compared with that of the maximum pore size layer on the surface of the membrane, and it was found that the anisotropic ratio was about 1 : 8 (the membrane was referred to as membrane B).

The same solution as descried above was cast. The cast film was exposed to air at 25° C. and 60% RH for 5 seconds, and immersed in water at 45° C. to obtain an anisotropic micro-filter membrane having a dense layer in the interior thereof. The pore size of the membrane was measured according to ASTM-F316. The average pore size was 1.5 μm. The cross-sectional SEM photograph was taken. The average pore size of the minimum pore size layer was compared with that of the maximum pore size layer on the surface of the membrane, and it was found that the anisotropic ratio was about 1 : 15 (the membrane was referred to as membrane C).

Figure 11:
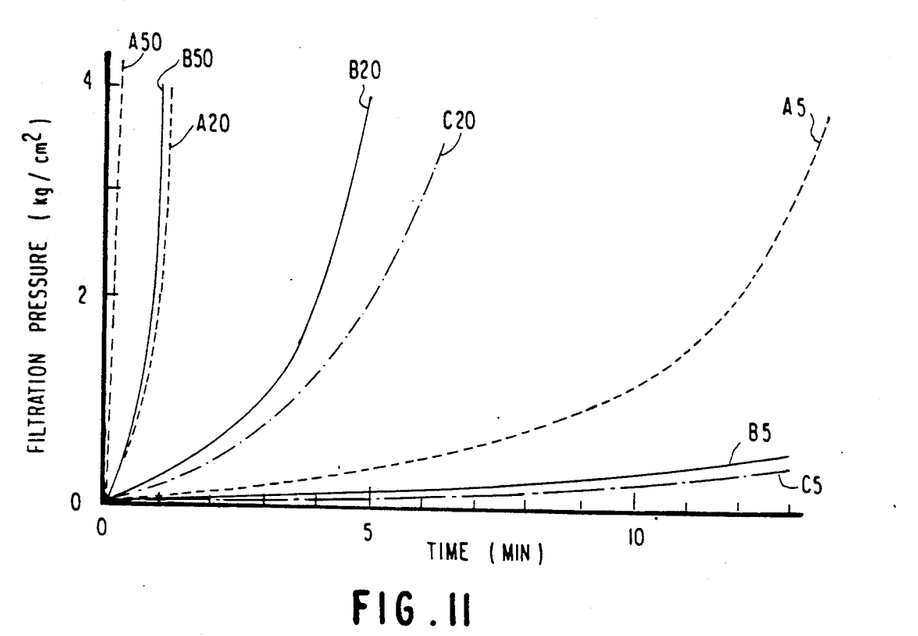
FIG. 11 is a graph showing curves for the comparison of filtration pressure increase when Hefeweizen bier is filtered by changing the anisotropy of the filter membrane and the flux (the signs in Fig. are illustrated in Table 1).

Hafeweizen Bier (Oberdorfer, Germany) was analyzed, and it was found that the total amount of suspended matter was 0.27 g/L, the number of yeast was 5×10$^3$/L, agglomerated polysaccharide content was 35 mg/L, agglomerated protein content was 70 mg/L, and the size of yeast was about 5 μm. This beer was used as a bulk solution to be filtered, and filtered through each of two membranes prepared above and NP membrane having a homogeneous structure (average pore size: 1.4 μm, the membrane was referred to as membrane A, manufactured by Pall Co.) under such conditions that the filtrate flux was 50 L/m$^2$·min, 20 L/m$^2$·min and 5 L/m$^2$·min. The curve of filtration pressure increase was measured. The results are shown in FIG. 11. The signs in FIG. 11 are illustrated in the following Table 2.

TABLE 2

| No. | Sign of Membrane | Filtrate Flux (l/m² · min) |
|---|---|---|
| A50 | A | 50 |
| A20 | A | 20 |
| A5 | A | 5 |
| B50 | B | 50 |
| B20 | B | 20 |
| B5 | B | 5 |
| C20 | C | 20 |
| C5 | C | 5 |

EXAMPLE 7

Figure 12:
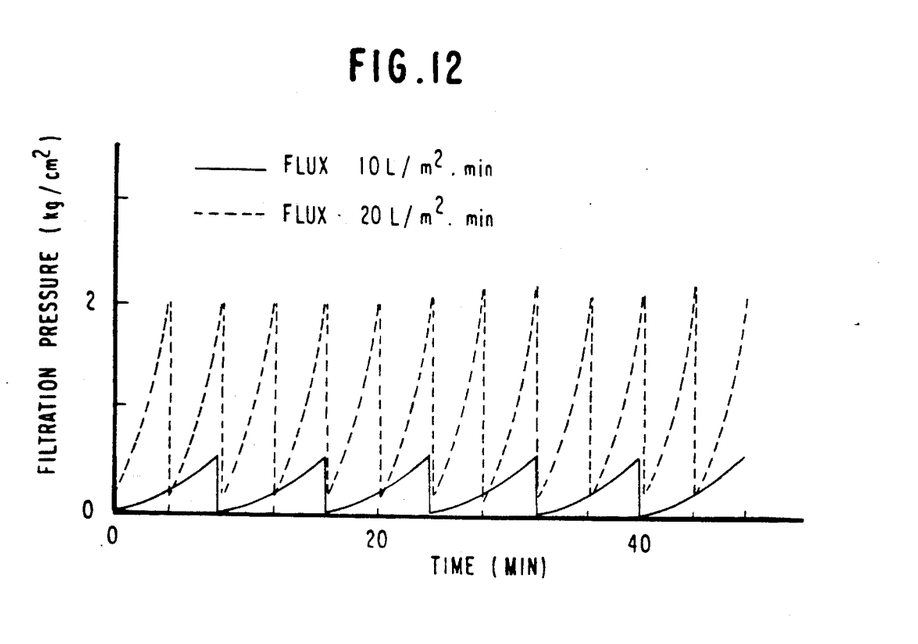
FIG. 12 is a graph showing the curves of filtration pressure increase when Hefeweizen bier is filtered while back wash is periodically carried out.

The same Hefeweizen Bier as described in Example 6 was filtered through the membrane prepared in Example 6 while back wash was repeated under the following conditions. FIG. 12 is a graph showing the results obtained by carrying out filtration at a filtrate flux of 10 L/m²·min for 3 seconds at intervals of 8 minutes while conducting back wash, and the results obtained by carrying out filtration at a filtrate flux of 20 L/m²·min for 3 seconds at intervals of 4 minutes while conducting back wash. The back wash was conducted by using water with a flux of 200 L/m²·min.

It is apparent from the above results that the anisotropic ratio of the pore size of the membrane and the filtrate flux have much effect on the rate of the filtration pressure increase, and a large amount of the liquid can be filtered when periodic back wash is conducted.

EXAMPLE 8

Figure 13:
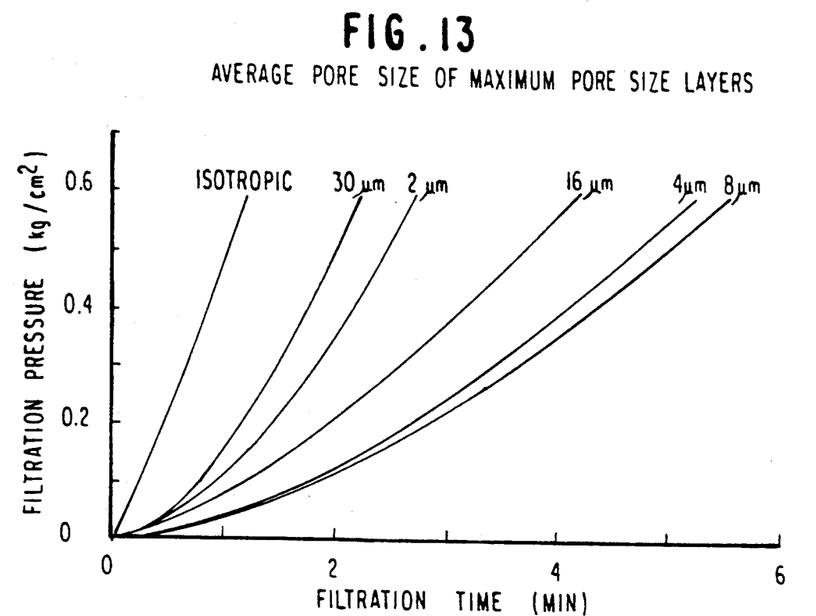
FIG. 13 is a graph showing curves for the comparison of filtration pressure increase when a cultured liquor of E. coli is filter by changing pore size on the surface of the filter membrane, said surface being first brought into contact with the bulk to be filtered.
Figure 14:
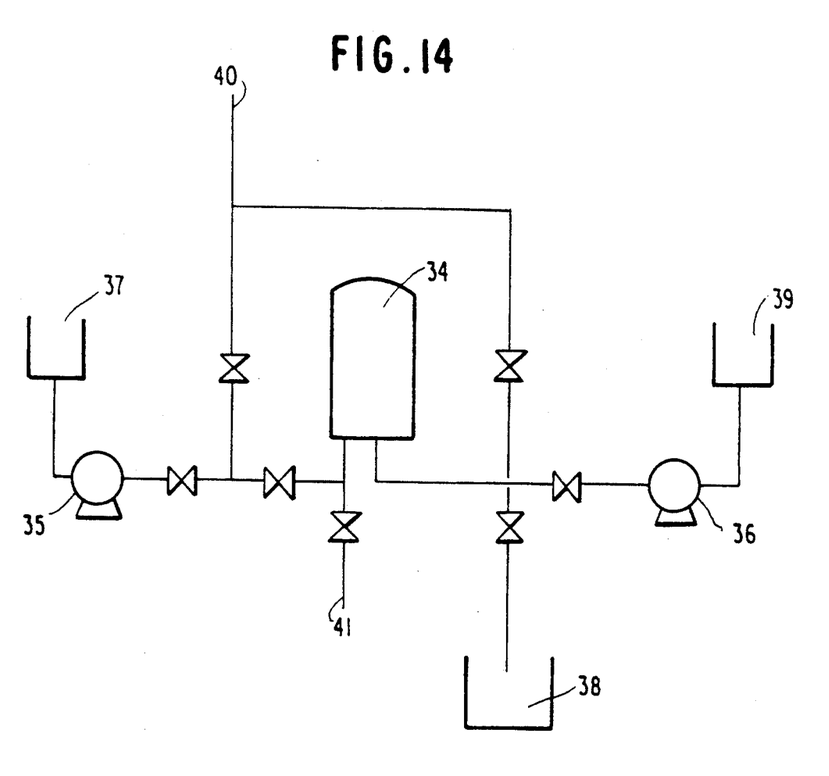
FIG. 14 is another flow sheet showing a dead-end type filtration system wherein back wash is periodically carried out according to the present invention.

Five membranes wherein the average pore size of the minimum pore size layer was 0.4 μm and the average pore sizes of the maximum pore size layers on the surface thereof ranged from 2 μm to 30 μm, were prepared in the same manner as in Example 6. The same *E. coli* cultured liquor as in Example 1 was used as the bulk solution to be filtered. The time of filtration pressure increase was measured. The results are shown in FIG. 13. For the purpose of comparison, an isotropic membrane (polyvinylidene fluoride, 0.4 μm, manufactured by Millipoa Corporation, Bedford, Mass.) was measured at the same time.

It is apparent from FIG. 13 that the rate of the filtration pressure increase of the anisotropic membranes having the maximum pore size layer having an average pore size of lager than 2 μm is slower than that of the filtration pressure increase of the isotropic membrane. The membranes having the maximum pore size layer having an average pore size of 4 μm and 8 μm are particularly suitable for use in the filtration of *E. coli* having a diameter of 0.6 μm and a length of 1 to 2 μm. It is also suggested that filtration can be effectively made when the dead-end type filtration is conducted while back wash is periodically carried out.

According to the present invention, a high filtrate flux through the membrane can be obtained in the dead-end type filtration system with periodic back wash, and the separation, recovery, purification and concentration of suspended components from liquids containing various suspended materials can be made effectively and economically. The continuous operation of the process and the miniaturization of devices can be made. Only the desired material can be separated continuously and selectively by utilizing the selectivity of the membrane. The present invention can be applied to bioreactors for yeast and cells and has such effects that operation and handling can be easily made in comparison with conventional technique.

While the invention has been described in detail and with reference to specific embodiments thereof, it will be apparent to one skilled in the art that various changes and modifications can be made therein without departing from the spirit and scope thereof.

What is claimed is:

1. In a dead-end type filtration system wherein a bulk comprising a fluid containing suspended matter is filtered through a micro-filter membrane to separate the fluid from the suspended matter, back wash is periodically carried out under such conditions that the pressure on the transmitted fluid side of the filter membrane is higher than the pressure on the bulk side thereof, and back wash liquid together with the suspended matter desorbed from the filter membrane is discharged from the filtration system to the outside, the filtration system is characterized in that the filter membrane has an anisotropic structure where the pore diameters of the filter membrane are changed continuously or discontinuously in the thickness direction of the filter membrane, the pore size of the densest layer of the membrane is in the range of from 0.05 to 10 μm, and the pore diameters on one side of the filter membrane are different from those on the other side thereof.

2. A filtration system as in claim 1, wherein the average pore size of the larger pore size surface side of the filter membrane is at least twice, but not larger than 500 times the average pore size of the densest layer present in the interior of the membrane.

3. A filtration system as in claim 2, wherein the pure water filtrate flux of said filter membrane at 25° C. is at least $1 \times 10^{-4}$ m³/m²/sec/atm.

4. A filtration system as in claim 1, wherein said filter membrane is arranged so that the larger pore size surface side thereof is positioned as the bulk side.

5. In a dead-end type filtration system wherein a bulk comprising a fluid containing suspended matter is filtered through a micro-filter membrane to separate the fluid from the suspended matter, back wash is periodically carried out under such conditions that the pressure on the transmitted fluid side of the filter membrane is higher than the pressure on the bulk side thereof, and back wash liquid together with the suspended matter desorbed from the filter membrane is discharged from the filtration system to the outside, the filtration system is characterized in that a filter membrane is used having a composite structure formed by integrating a micro-filter membrane with nonwoven fabric or a network structural material, the filter membrane has an anisotropic structure where the pore diameters of the filter membrane are changed continuously or discontinuously in the thickness direction of the filter membrane, the pore size of the densest layer of the membrane is in the range of from 0.05 to 10 μm, and the pore diameters on one side of the filter membrane are different from those on the other side thereof.

6. A filtration system as in claim 5, wherein the nonwoven fabric side or network structural material side of filter membrane is positioned as the bulk side.

7. A filtration system as in claim 5 or 6, wherein the pure water filtrate flux of said filter membrane at 25° C. is at least $1 \times 10^{-4}$ m³/m²/sec/atm.

8. A dead-end type filtration method characterized in that (1) a micro-filter membrane is used having anisotropy in pore size in the thickness direction of the membrane wherein the pore size on the membrane surface which is first brought into contact with the bulk to be filtered is 2 to 20 times the volume average particle size of suspended particles in said bulk, the pore size of the densest layer of the membrane is in the range of from 0.05 to 10 μm, and the pore size of the densest layer of the membrane is not larger than 0.8 times the particle size of the particles to be removed, and (2) back wash is periodically carried out under such conditions that pressure on the transmitted fluid side of the filter membrane is higher than pressure on the bulk side when the filter membrane is clogged, and the back was liquid together with the suspended matter desorbed from the filter membrane is discharged from the filtration system to the outside.

9. A filtration method involving periodic back wash as in claim 8, wherein the pore size on the membrane surface which is first brought into contact with the bulk to be filtered is 4 to 30 μm, the pore size of the densest layer of the membrane is 0.3 to 3 μm, and the bulk to be filtered is a fermented alcoholic suspension.

10. A filtration method involving periodic back wash as in claim 8, wherein the fermented alcoholic suspension is beer and filtered at a flux of not higher than 20 $L/m^2 \cdot min$.

* * * * *